US008360376B2

(12) United States Patent
Gawelek et al.

(10) Patent No.: US 8,360,376 B2
(45) Date of Patent: Jan. 29, 2013

(54) ARTICULATING MOUNT

(75) Inventors: Marcin Gawelek, Aurora (CA); Ryan Theakston, London (CA)

(73) Assignee: Oasys Healthcare Corporation, Uxbridge (CA)

( * ) Notice: Subject to any disclaimer, the term of this patent is extended or adjusted under 35 U.S.C. 154(b) by 222 days.

(21) Appl. No.: 12/851,294

(22) Filed: Aug. 5, 2010

(65) Prior Publication Data

US 2011/0031357 A1 Feb. 10, 2011

Related U.S. Application Data

(60) Provisional application No. 61/231,496, filed on Aug. 5, 2009.

(51) Int. Cl.
*E04G 3/00* (2006.01)
(52) U.S. Cl. .......... 248/292.11; 248/123.11; 248/280.11
(58) Field of Classification Search ................. 248/129, 248/123.11, 372.1, 162.1, 276.1, 278.1, 280.11, 248/292.11
See application file for complete search history.

(56) References Cited

U.S. PATENT DOCUMENTS

| | | | | |
|---|---|---|---|---|
| 4,166,602 A * | 9/1979 | Nilsen et al. | ............. | 248/280.11 |
| 4,832,294 A * | 5/1989 | Eidem | ........................ | 248/125.8 |
| 5,004,368 A | 4/1991 | Warga | ............................ | 403/166 |
| 5,344,169 A * | 9/1994 | Pryor et al. | .................... | 280/79.3 |
| 5,918,841 A * | 7/1999 | Sweere et al. | ............ | 248/123.11 |
| 5,975,472 A * | 11/1999 | Hung | .......................... | 248/278.1 |
| 5,987,670 A * | 11/1999 | Sims et al. | ......................... | 5/600 |
| 6,012,821 A | 1/2000 | Yeaney et al. | .................. | 362/33 |
| 6,070,839 A * | 6/2000 | Brenner et al. | .......... | 248/123.11 |
| 6,164,612 A | 12/2000 | Schmitt | ..................... | 248/280.11 |
| 6,261,023 B1 | 7/2001 | Schmitt et al. | ................... | 403/91 |
| 6,328,458 B1 | 12/2001 | Bell et al. | ....................... | 362/371 |
| 6,394,403 B1 * | 5/2002 | Hung | .......................... | 248/276.1 |
| 6,398,172 B1 | 6/2002 | Rousek et al. | ................ | 248/121 |
| 6,793,380 B2 | 9/2004 | Kupfer | ........................... | 362/371 |
| 7,207,537 B2 * | 4/2007 | Hung | .......................... | 248/284.1 |
| 7,255,311 B2 * | 8/2007 | Metelski | .................. | 248/123.11 |
| 7,338,022 B2 * | 3/2008 | Hung | ......................... | 248/278.1 |
| 7,540,457 B2 * | 6/2009 | Oddsen et al. | ................ | 248/278.1 |
| 7,748,666 B2 * | 7/2010 | Oddsen et al. | ............ | 248/123.11 |
| 7,798,456 B2 * | 9/2010 | Newkirk et al. | ............ | 248/219.1 |
| 2005/0139736 A1 * | 6/2005 | Breda et al. | .................. | 248/129 |
| 2007/0040084 A1 * | 2/2007 | Sturman et al. | .......... | 248/280.11 |

* cited by examiner

*Primary Examiner* — Bradley Duckworth
(74) *Attorney, Agent, or Firm* — Jonathan M. D'Silva; David S. Willoughby; MacDonald, Illig, Jones & Britton LLP

(57) ABSTRACT

An articulating mount has a hollow support arm with a compression spring inside of it. The spring is on a threaded rod and held at one end by a nut. At the other end, the spring rests against a washer. The washer rests against an indentation in the tube. One end of the threaded rod is connected via rotation links to an adjustment cross inside a housing. The housing has a threaded captive adjustment screw that is attached to both the housing by way of an adjustment pin and to the adjustment cross by its external threading. The housing is secured to a steel support body.

13 Claims, 15 Drawing Sheets

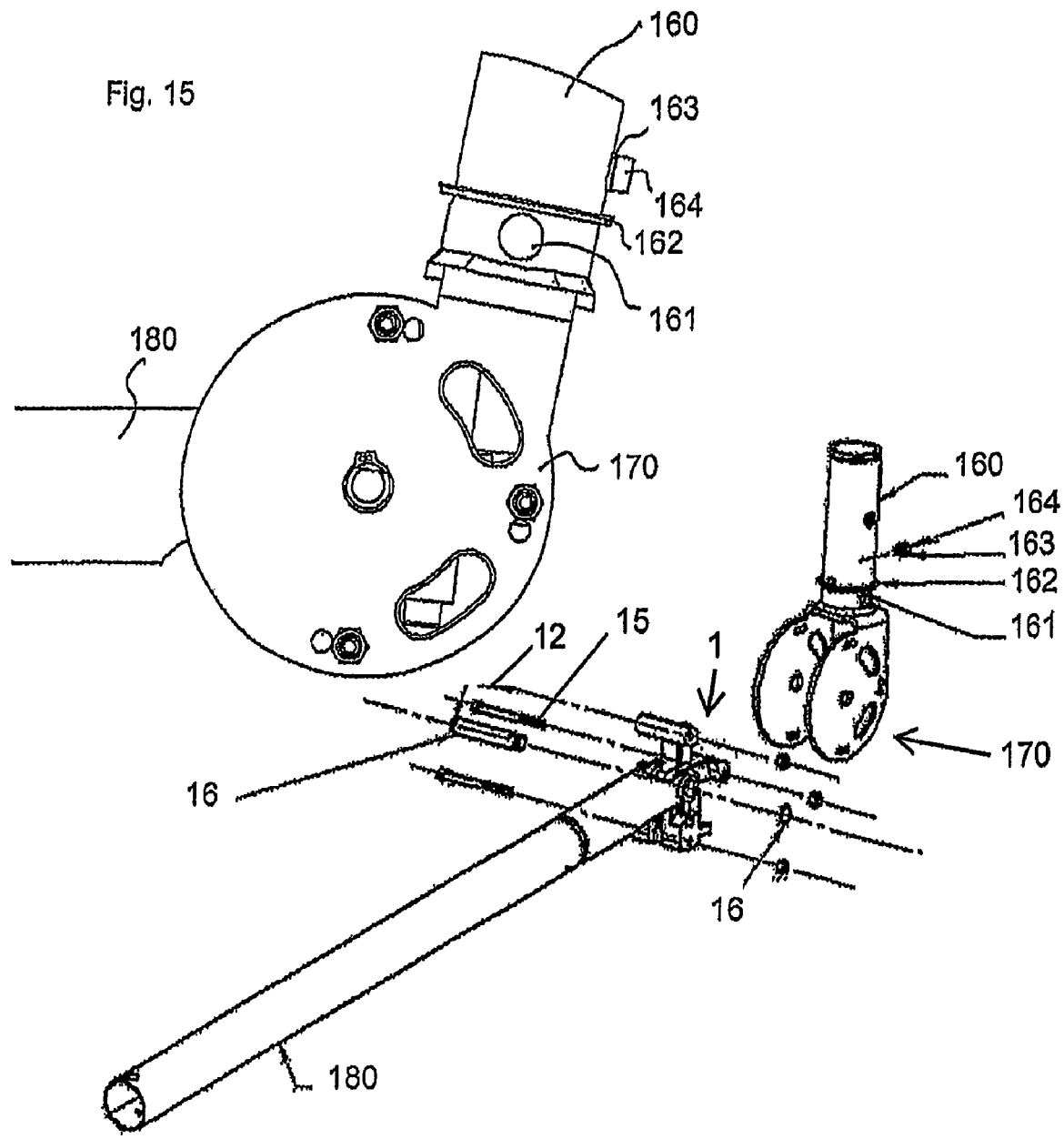

ARTICULATING MOUNT

RELATED APPLICATIONS

This application claims priority to U.S. Provisional Patent Application Ser. No. 61/231,496 filed on Aug. 5, 2009, which is hereby incorporated by reference in its entirety.

FIELD OF THE INVENTION

The invention relates generally to load support systems. In particular, the invention relates to articulating mounts, such as those in healthcare support systems.

BACKGROUND

An articulating mount has a spring in compression, inside an arm attached to a point of rotation. It functions to counter balance the weight of an apparatus mounted to it and allow the user to comfortably raise and lower the mounted apparatus as desired and have it remain in the same position without the need to perform any additional steps to keep the articulated mount from moving.

Articulating mounts are commonly used to support relatively light weight medical apparatuses in hospitals, medical offices, nursing homes, long term care, and other healthcare facilities and environments. Common relatively light weight medical apparatuses include, but are not limited to, sensors, lights, flat screen monitors, x-ray projections systems and cameras.

Of course, articulating mounts are also used in other industries besides the healthcare industry, including for example, hair salons, spas, retail fixtures, information technology, etc. The mounted apparatuses can include hair dryers, televisions, computers, retail product displays and samples, commercial presentation material, etc.

Previous articulating mounts for medical apparatuses are bulky, costly as well as labor intensive in their assembly. Many articulating mounts also have arms which are off-set, such as those in U.S. Pat. No. 6,261,023. Their functionality is also reduced due to their complexity, multitude of parts, and decreased reliability. In particular, the articulating mounts of many healthcare support systems are moved quite often and may unacceptably fail when rotating components in the mount become worn. When an articulating mount fails, the supported apparatus may suddenly or unexpectedly drop, causing damage to the apparatus and potential harm to a patient depending on the functions performed by the apparatus.

BRIEF SUMMARY OF THE PREFERRED EMBODIMENTS

The preferred embodiments of the invention include an articulating mount for apparatuses, particularly, but not limited to, supporting medical apparatuses, that have improved functionality, improved assembly, fewer parts and better reliability, thereby reducing the overall cost and improving performance.

BRIEF DESCRIPTION OF THE DRAWINGS

For a more complete understanding and appreciation of the preferred embodiments of the invention, and its many advantages, reference will be made to the following detailed description of the preferred embodiments taken in conjunction with the accompanying drawings.

FIG. 11 is an exploded view showing the final assembly of the articulating mount according to the preferred embodiment of the invention.

FIG. 15 is a side view of the housing in the complete articulating mount according to the preferred embodiment of the invention.

DETAILED DESCRIPTION OF THE PREFERRED EMBODIMENTS

Figure 1A:
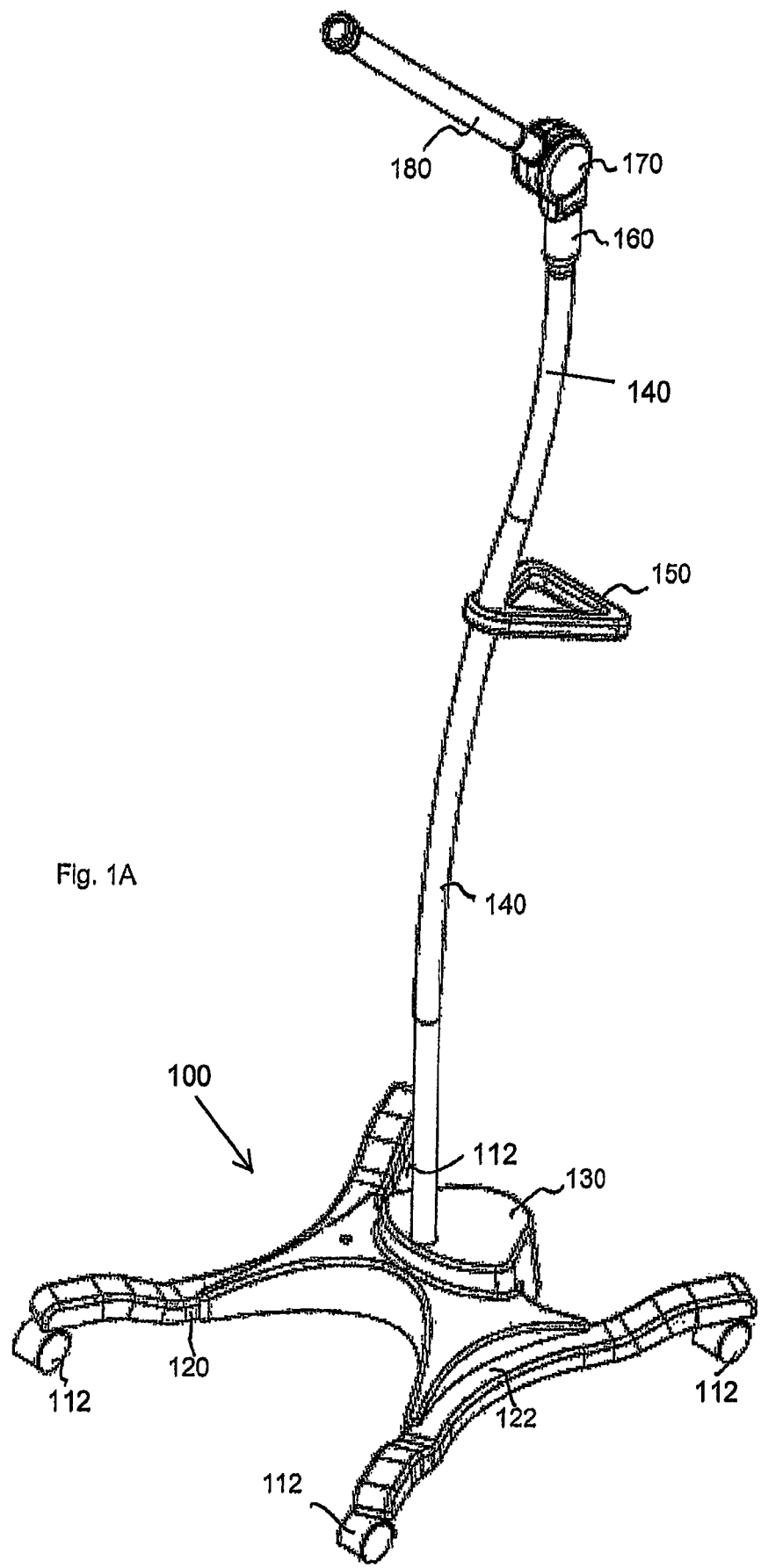
FIG. 1A is a perspective view of a floor support stand with an articulating mount according to a preferred embodiment of the invention.

Referring to the drawings, some of the reference numerals are used to designate the same or corresponding parts through several of the preferred embodiments and figures shown and described. Variations of corresponding parts in form or function that are depicted in the figures are described. It will be understood that variations in the preferred embodiments can generally be interchanged without deviating from the invention.

The preferred embodiments of the invention may take form in various components and arrangements of components, and in various steps and arrangements of steps. The drawings are only for the purposes of illustrating a preferred embodiment and are not to be construed as limiting the invention.

Figure 1B:
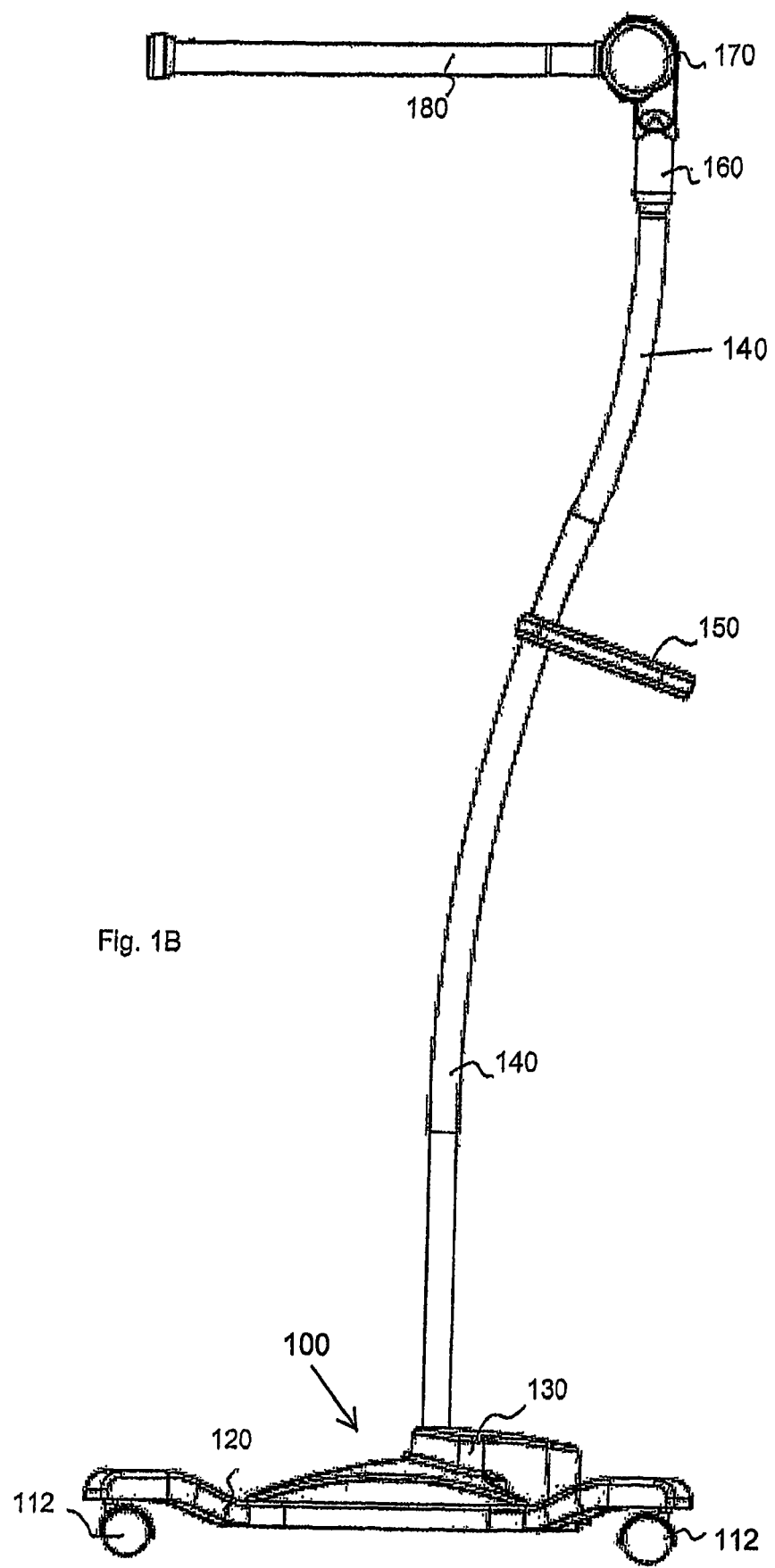
FIG. 1B is a side view of the floor support stand in FIG. 1.
Figure 1C:
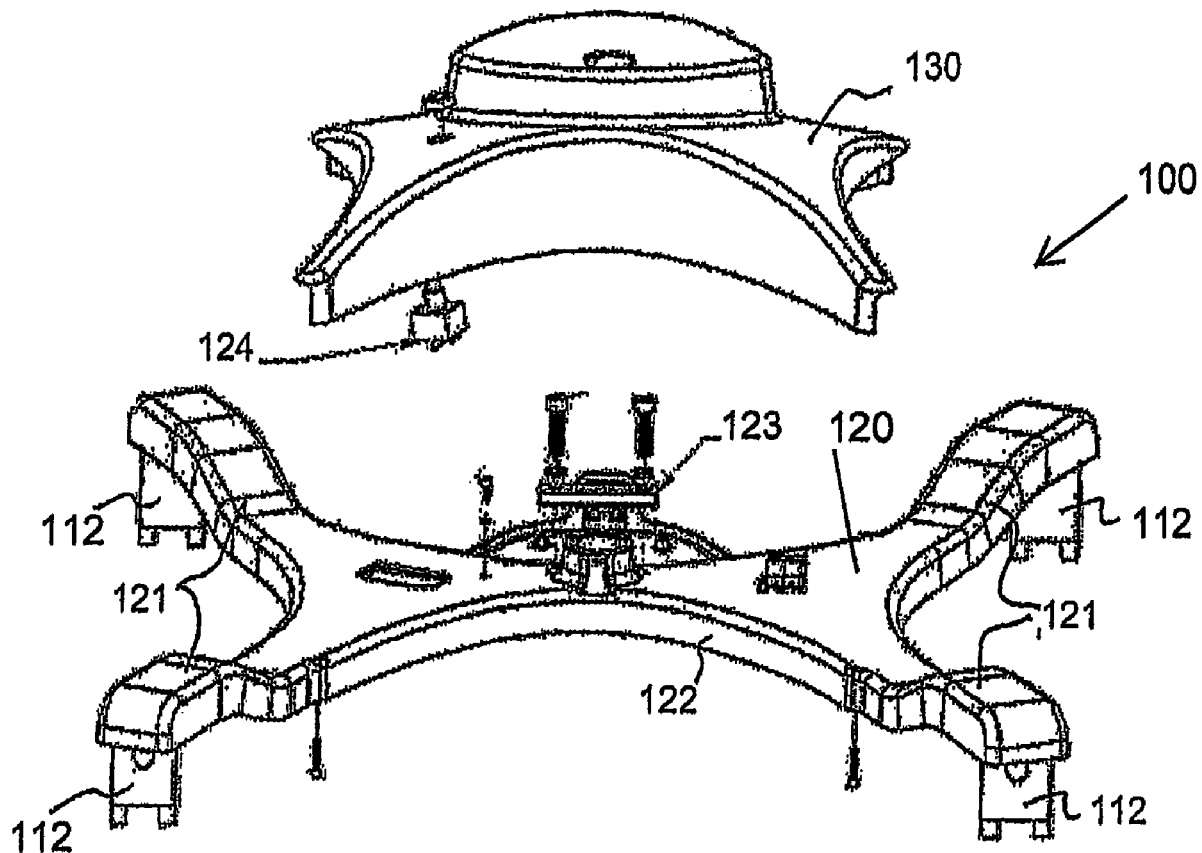
FIG. 1C is a perspective view of the base assembly in the floor support stand of FIG. 1.

The first preferred embodiment of the invention is the floor support stand 100 shown in FIGS. 1A-1C. The floor support stand 100 consists of four rolling wheels-112 supporting a base 120. A base cover 130 is attached to sunken central portion 122 of base 120 and encloses a transformer, fuses and other electronics used to provide power to the apparatus supported by floor support stand 100. For simplification, the drawings do not show the power supply cord and wires used to provide electricity to the apparatus supported by the floor support stand 100. A post 140 passes through base cover 130 and is attached to central portion 122 of base member 120. A handle 150 is secured to the post, preferably at a height that facilitates movement of the floor support stand 100 by personnel. Post 140 may be curved as shown in FIGS. 1A and 1B, may be curved in some other manner or may be straight. Although three post sections are shown in FIG. 1A, post 130 may have any number of post sections. A support body 160 at the top of post 140 supports an articulating mount 170 which permits support arm 180 to be rotated in the vertical direction and stay in a chosen position. The support arm 180 may be straight as shown in FIGS. 1A and 1B or it may be curved or bent. The articulating mount 170 is preferably concealed by one or more plastic covers.

FIG. 1C shows further details of the base member 120 and base cover 130. Base member 120 is preferably attached to the upper portions of the rolling wheels 112 by base supports 121, and has a central portion 122 that is sunken relative to the base supports 121. At least a part of the sunken central portion 122 is lower than the upper portions of the rolling wheels 112 to aid against accidental tipping of the floor support stand 100. Central portion 122 includes a post attachment bar 123 for attaching post 130 to base member 120. A push button switch 124 protrudes through a hole in the top of base cover 130 and acts to turn on (and off) power to the apparatus through wires fed through the interior of post 130 (not shown). The lower side of the upper surface of base cover 130 may include protruding tabs to ensure proper orientation of the switch 124.

Figure 2:
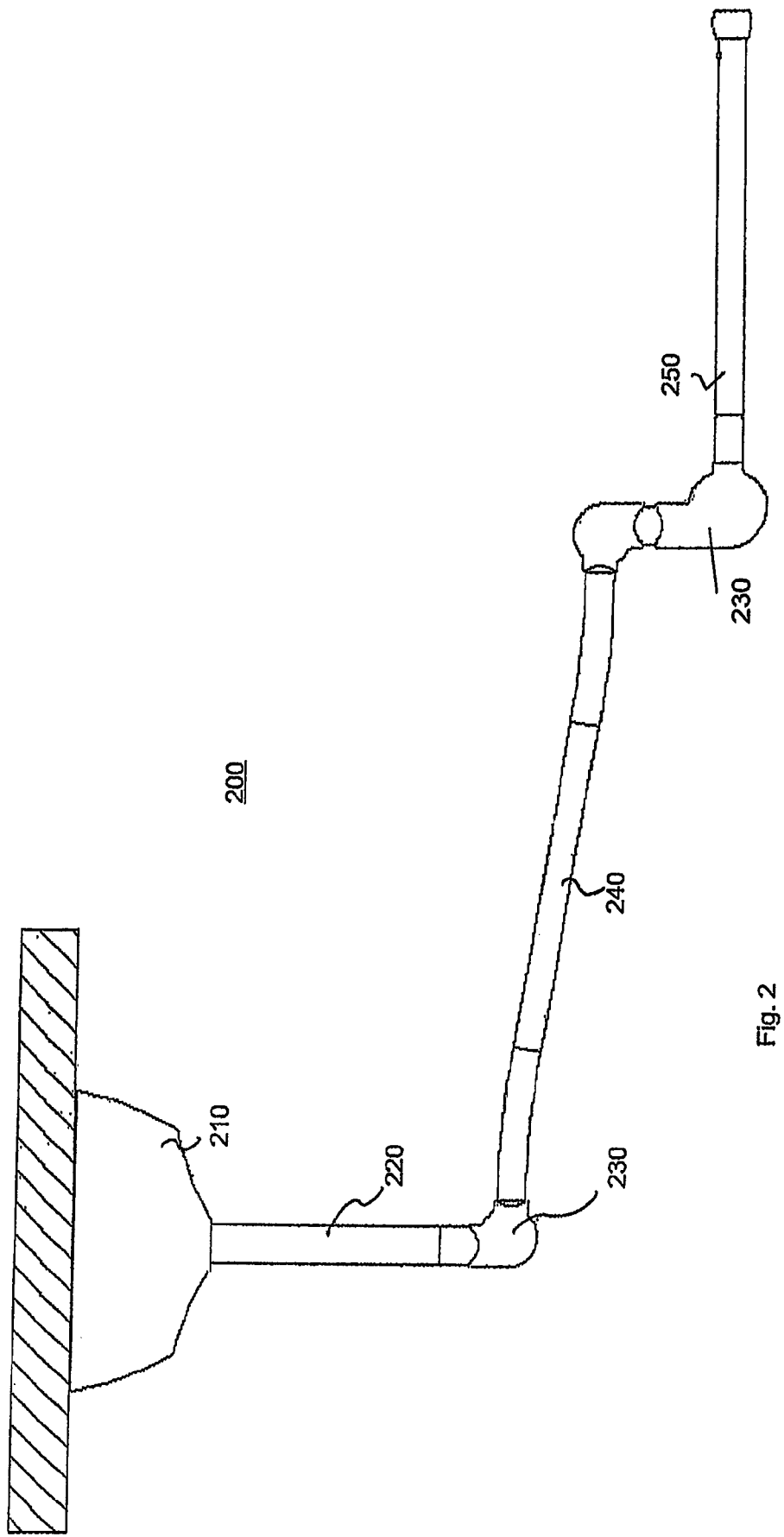
FIG. 2 is a side view of a wall support system with an articulating mount according to the preferred embodiment of the invention.
Figure 3:
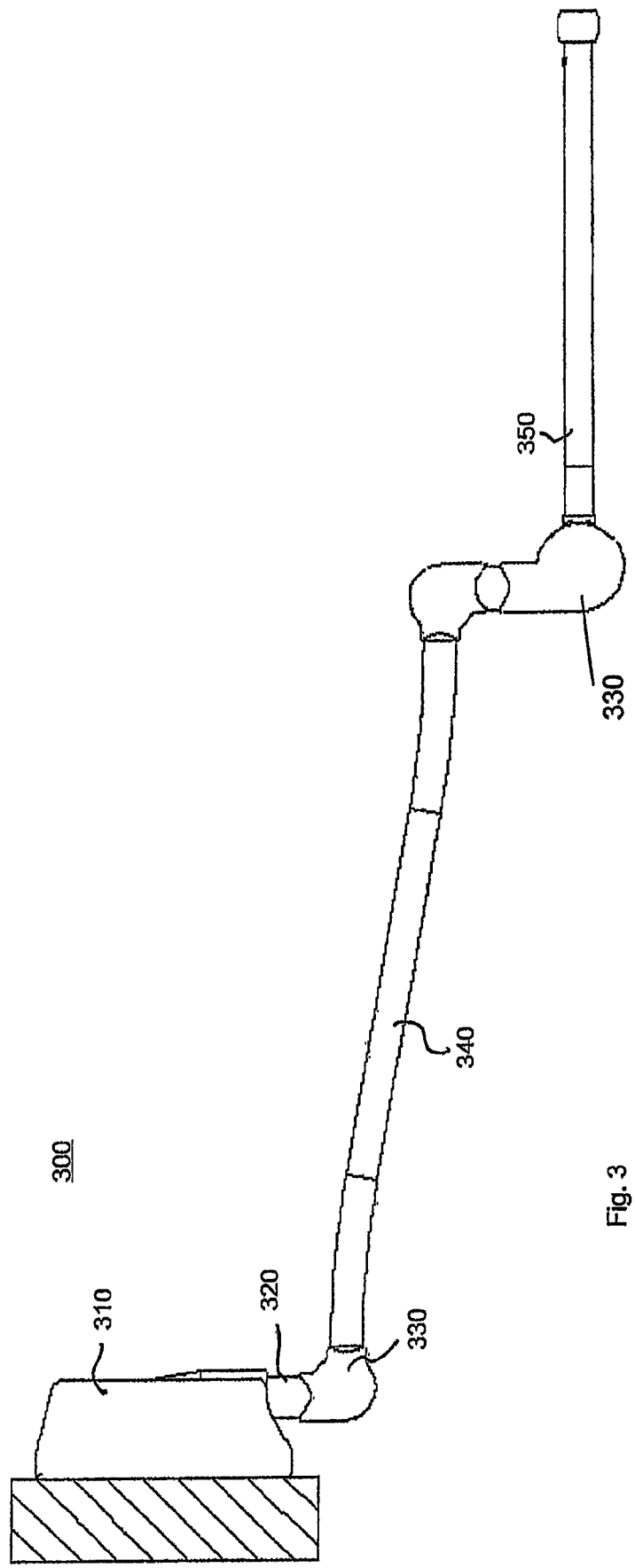
FIG. 3 is a side view of a ceiling support system with an articulating mount according to the preferred embodiment of the invention.

A wall mounted embodiment 200 and a ceiling mounted embodiment 300 are shown in FIGS. 2 and 3, respectively. Wall mount 200 includes a mounting base (with cover) 210, retaining an extension arm 220 extending from mounting base 210. Similarly, ceiling mount 300 includes a mounting base (with cover) 310, retaining an extension arm 320 extending from mounting base 310. The extension arms 220, 320 may be stationary or pivoting. An articulating mount 230, 330 connects the extension arm 220, 320 to post sections 240, 340. Two further articulating mounts 230, 330 connect the post section to a support arm 250, 350. Although FIGS. 2 and 3 show particular wall mounted and ceiling mounted embodiments, different configurations may be employed as well.

The articulating mount 170 will now be described with reference to FIGS. 4-17. The spring assembly in the support arm is illustrated in FIG. 8. The threaded rod 6 has a notched end 7 whose outer circumference is larger than the outer circumferences of the remainder of the threaded rod 6. The notched end 7 may be integrally formed with threaded rod 6 or may be a linkage bracket welded to threaded rod 6. In either case, the notched end has a rectangular notch 7-1 with two opposing spring pin holes 7-2. Compression spring 2 has an inner circumference which is slightly greater than the outer circumference of the threaded rod 6 and surrounds threaded rod 6.

One end of compression spring 2 abuts either the notched end 7 of threaded rod 6 or an indentation in the support arm 180. The compression spring 2 is separated from the indentation or notched end 7 by an oblong washer 4. Preferably, a spring bushing 4-1, a spring clamp ring 4-2 and a first spring end bushing 3 are further interposed between the oblong washer 4 and the compression spring 2. The flat side of the spring bushing 4-1 is flush with the oblong washer 4 and its shoulder is pointing away from the oblong washer 4. The spring clamp ring 4-2 preferably has a tapered hole, and the large end of the taper faces the oblong washer 4. The spring end bushing 3 has a flat side facing the spring clamp ring 4-2 and the other side is fitted to the compression spring 2.

The other end of the compression spring 2 opposite the notched end 7 is held in place by a threaded rod nut 5 on the end of the threaded rod 6. A second spring end bushing 3 is preferably between the compression spring 2 and the rod nut 5 with its flat side facing rod nut 5 and the other side fitted to compression spring 2. The rod nut 5 can be hand tight or tightened so that the compression spring 2 is compressed to a specific length.

Figure 4:
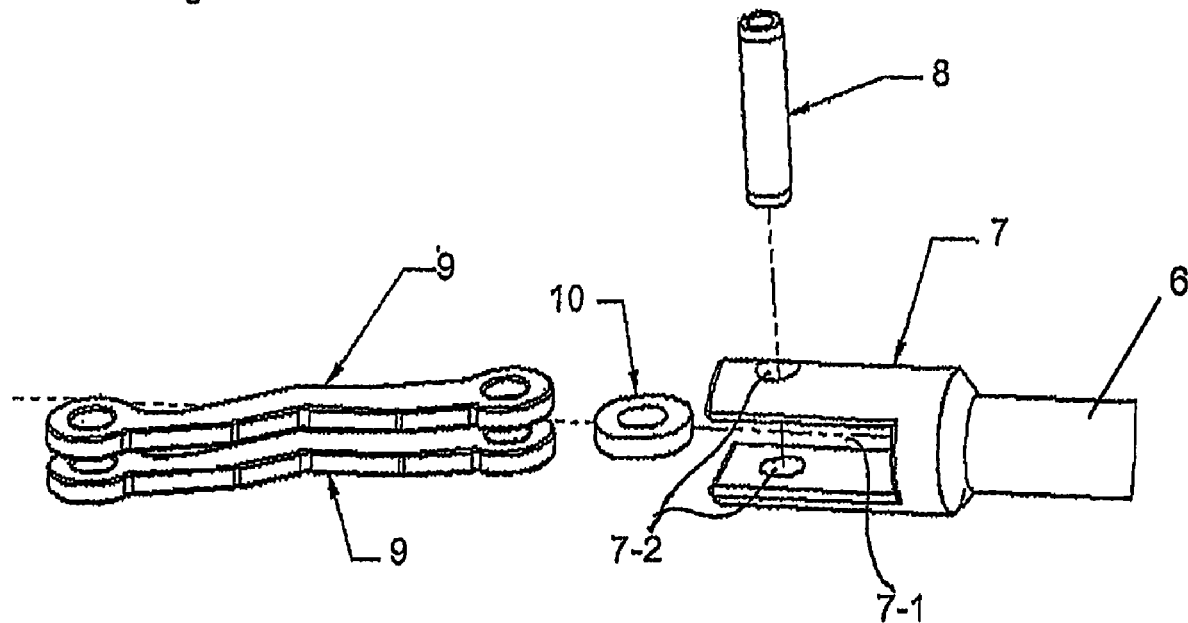
FIG. 4 is a diagram showing a disassembled spring pin assembly in the preferred embodiment of the articulating mount.

FIG. 4 shows the unassembled pieces which connect the notched end 7 of threaded rod 6 in the support arm 180 to the articulating mount 170 (both shown in FIG. 1A-1C) according to a preferred embodiment of the articulating mount. Two rotation links 9 separated by a link spacer 10 are located in the rectangular notch 7-1 so as to pivot freely. Each one of the rotation links 9 has a hole at each of its end. A coiled spring pin 8 through the link spacer and two spring pin holes 7-2 in the notched end of the threaded rod 7 and two pin bushings outside the notched end 7 secure the rotation links 9 to the notched end 7 of the threaded rod 6. Preferably, the rotation links have a pointing chevron (or other kind of kink) rather than being straight or uniformly curved.

Figure 5:
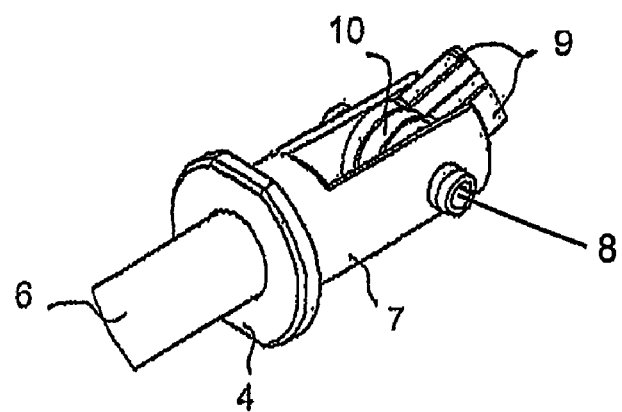
FIG. 5 is a diagram showing the spring pin assembly and spring washer in the preferred embodiment of the articulating mount.

The oblong washer 4 has an inner circumference so that it fits around the remainder of the threaded rod 6 but abuts against the larger diameter of the notched end 7 or an indentation inside the hollow support arm 180. The oblong washer 4 is orientated as illustrated in FIG. 5 so that the flat sides are parallel with the spring pin holes 7-2 and the chamfer is facing away from the arms of the notched end 7. The spring bushing 4-1, and the flats on the first and second spring end bushings 3, have the same orientation as the oblong washer 4.

The threaded rod 6 may be hollow to allow a cable or tube to go through it. This cable or tube is then routed through the notched end 7 from the same side of support arm 180 where the chevrons of the rotation links 9 are pointing up, after which it is routed through a steel cable bushing (not shown) which can slide in a slot in the articulating mount 170. This steel cable bushing is used to protect the cable or tube from wear due to the rubbing in the articulating mount 170. The cable or tube then routes into the second arm or mount 160 through a hole in the base of the second arm or mount 160, to the base 120 of floor stand 100 or the mount 210,310 of the wall or ceiling embodiments.

Figure 9:
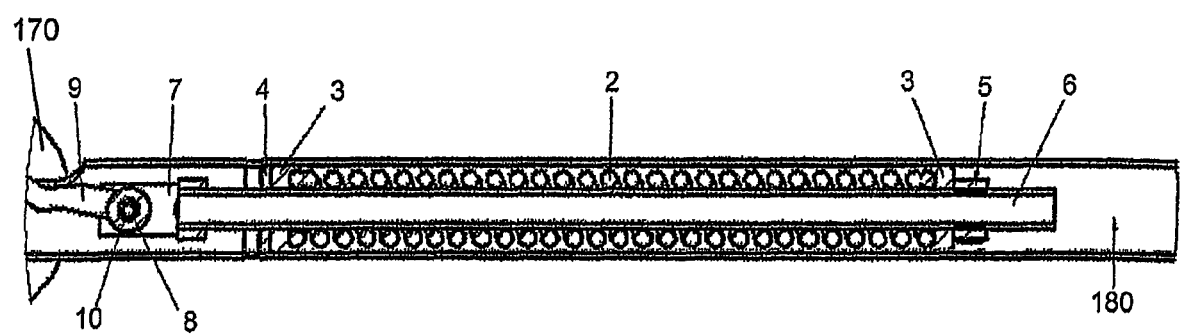
FIG. 9 is a cross-section side view of the tubular arm and its components in the preferred embodiment of the articulating mount.
Figure 12:
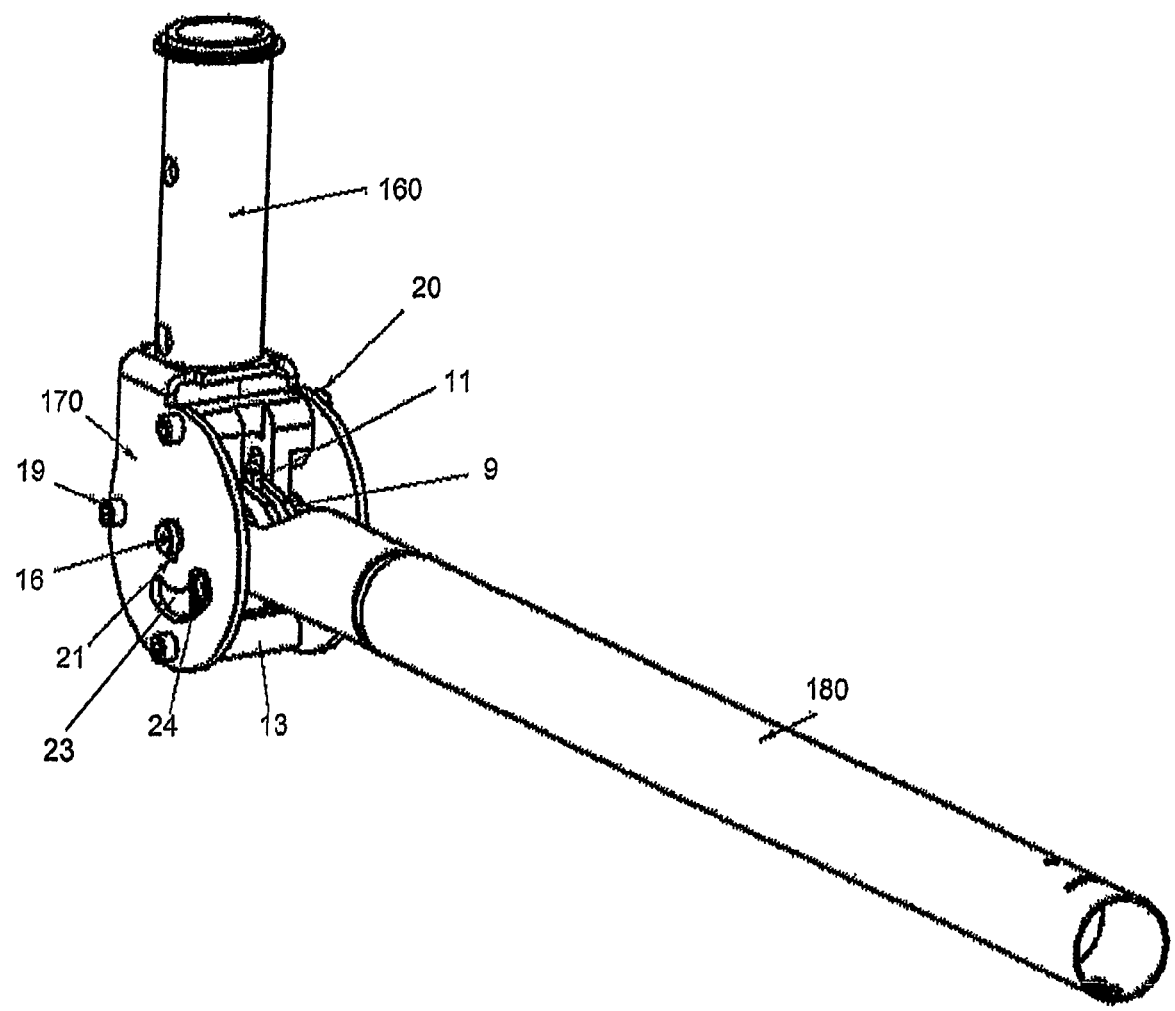
FIG. 12 is a front perspective view of the complete articulating mount according to the preferred embodiment of the invention.
Figure 13:
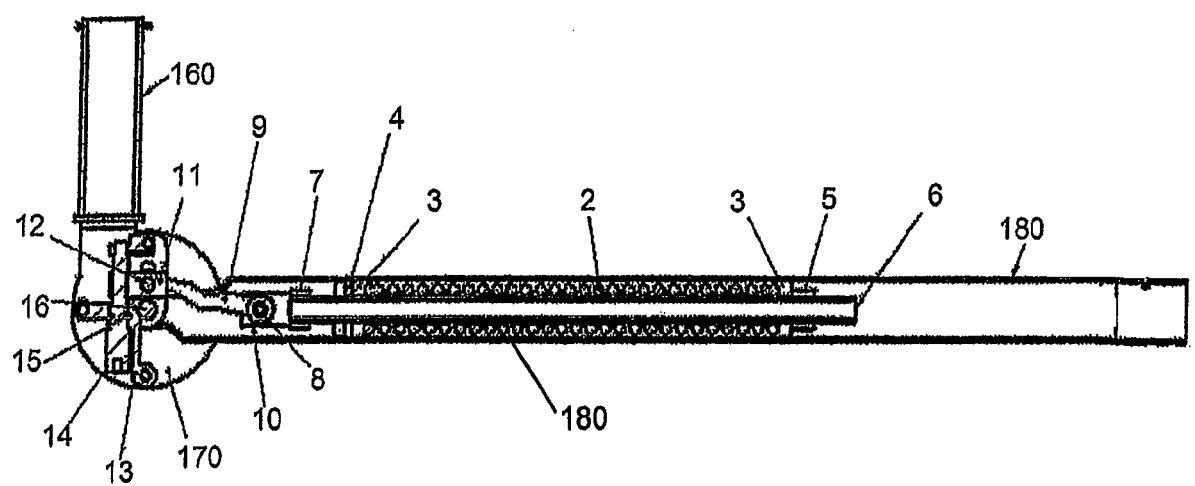
FIG. 13 is a cross-section side view of the complete articulating mount according to the preferred embodiment of the invention.
Figure 14:
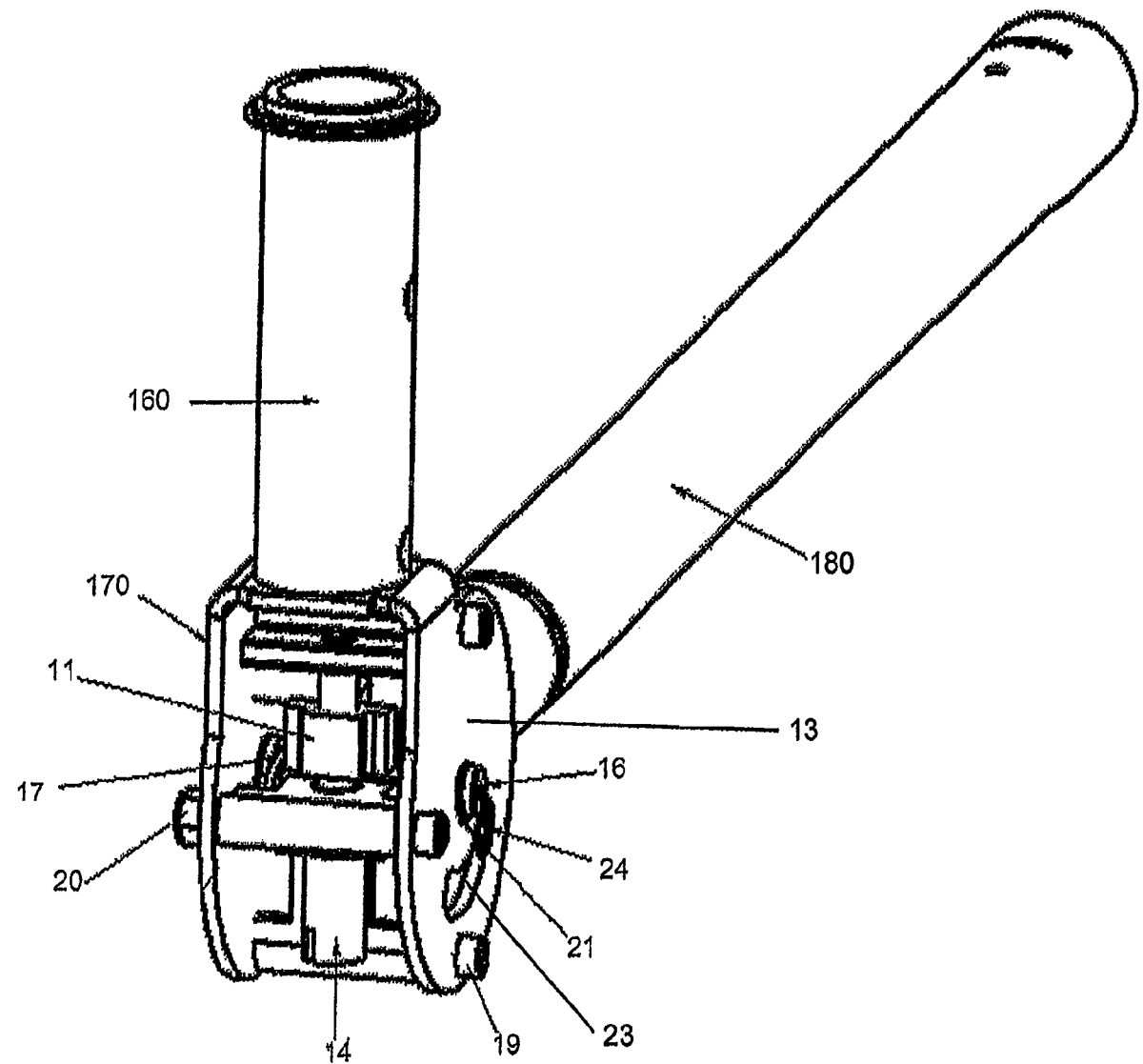
FIG. 14 is a rear perspective view of the complete articulating mount according to the preferred embodiment of the invention.
Figure 16:
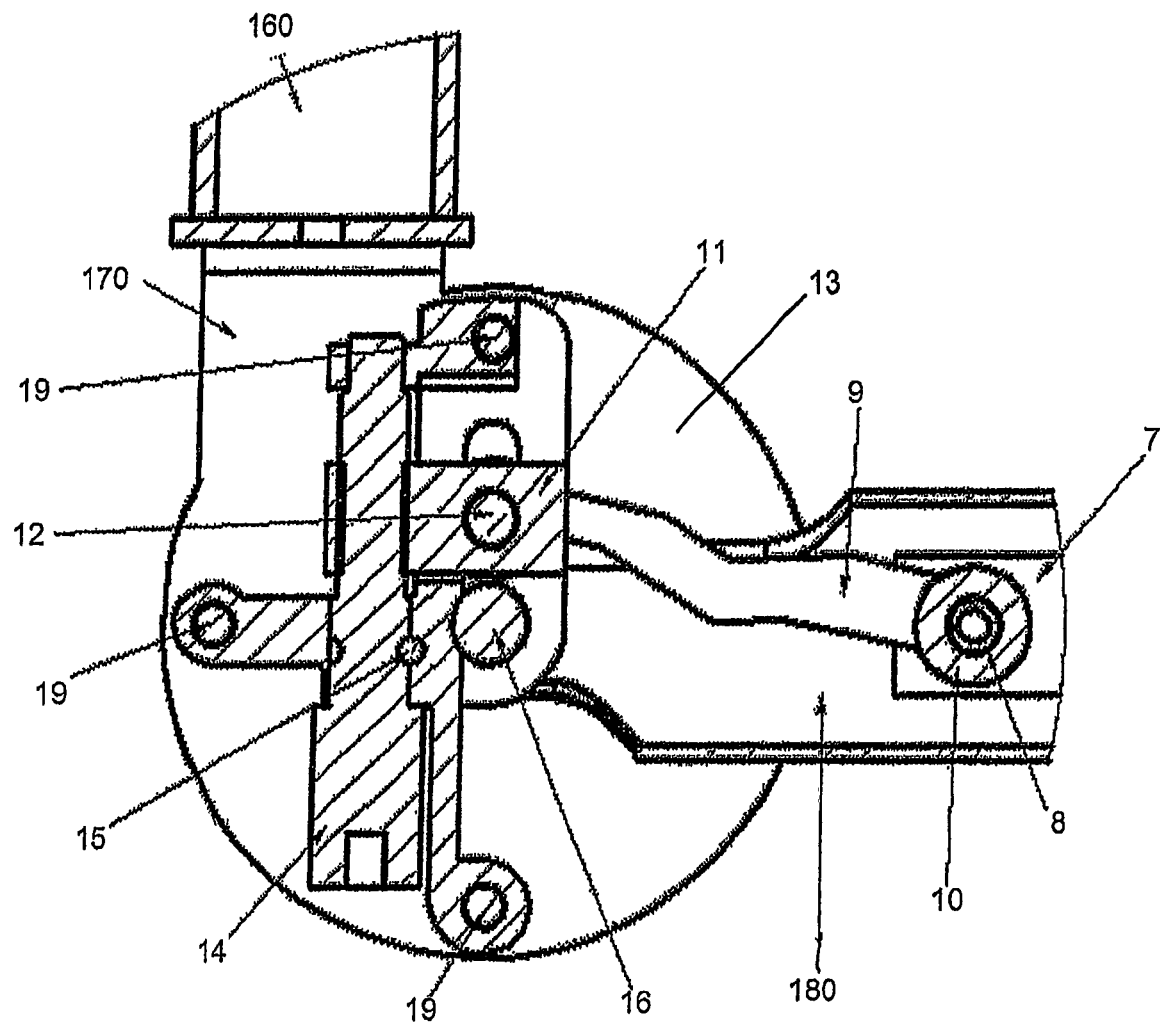
FIG. 16 is a cross-section side view of the body assembly and its components in the complete articulating mount according to the preferred embodiment of the invention.
Figure 17:
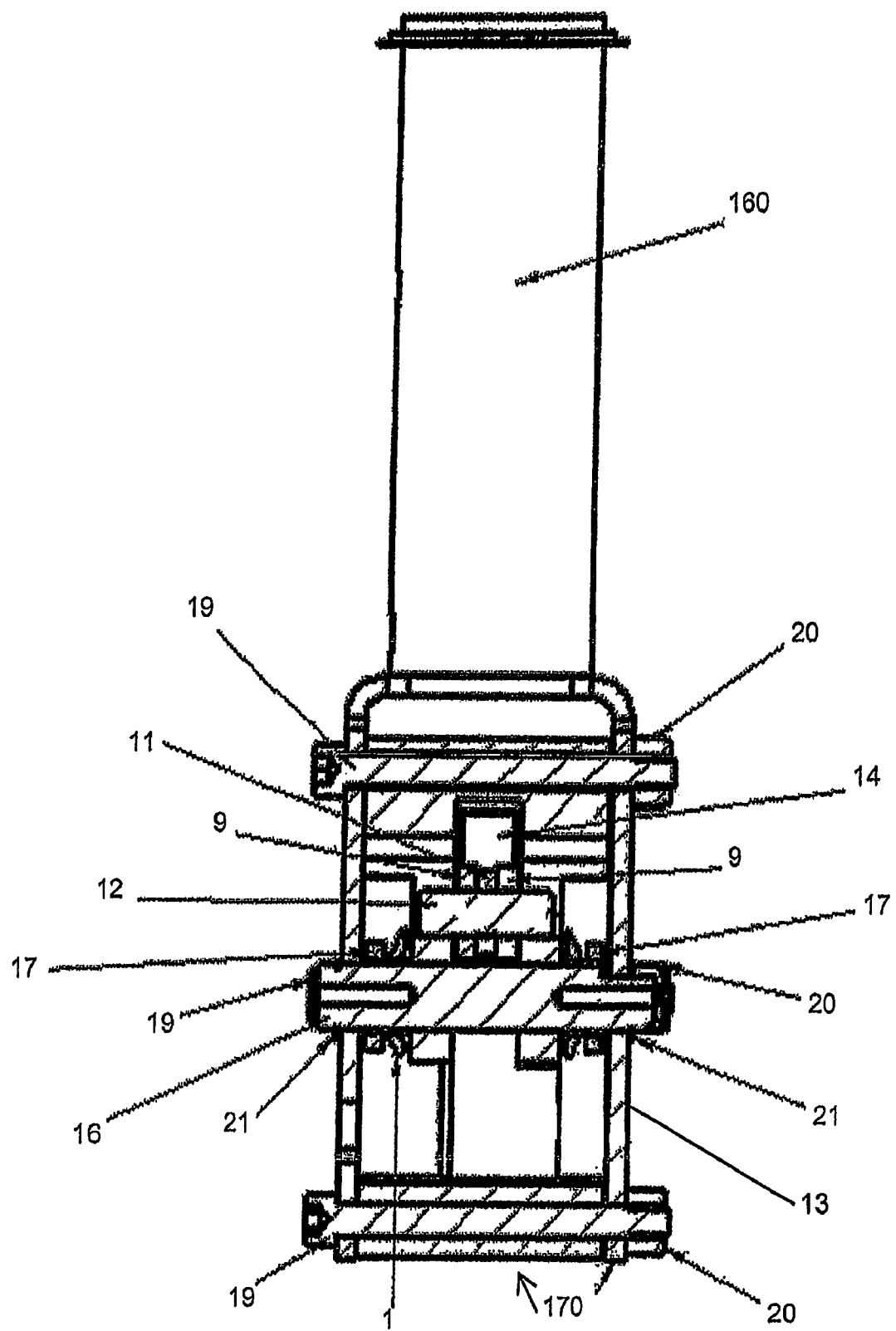
FIG. 17 is a cross-section front view through the center shaft of the articulating mount according to the preferred embodiment of the invention.

The components are located inside hollow support arm 180 as shown in FIGS. 9 and 13. FIG. 9 is a cross-sectional view of the components inside the support arm 180. FIG. 13 is a cross-sectional view showing the connection of the components inside support 180 to a main body in the articulating mount 170, as described in further detail below.

Figure 7:
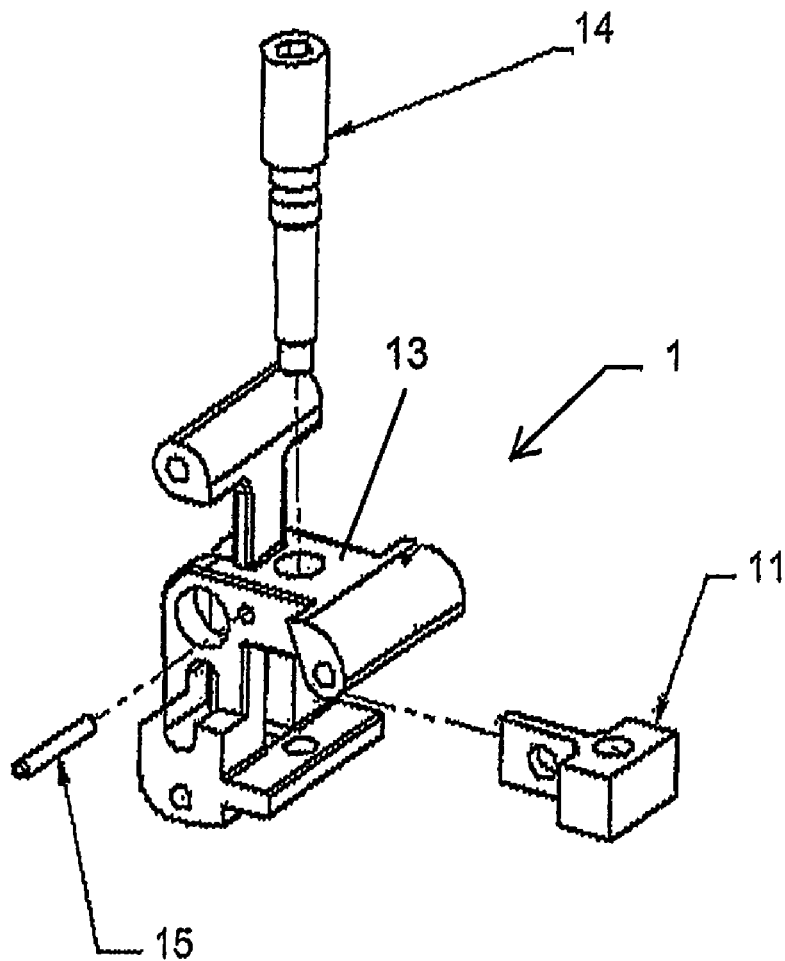
FIG. 7 is a diagram illustrating an exploded view of the body assembly in the preferred embodiment of the articulating mount.
Figure 6:
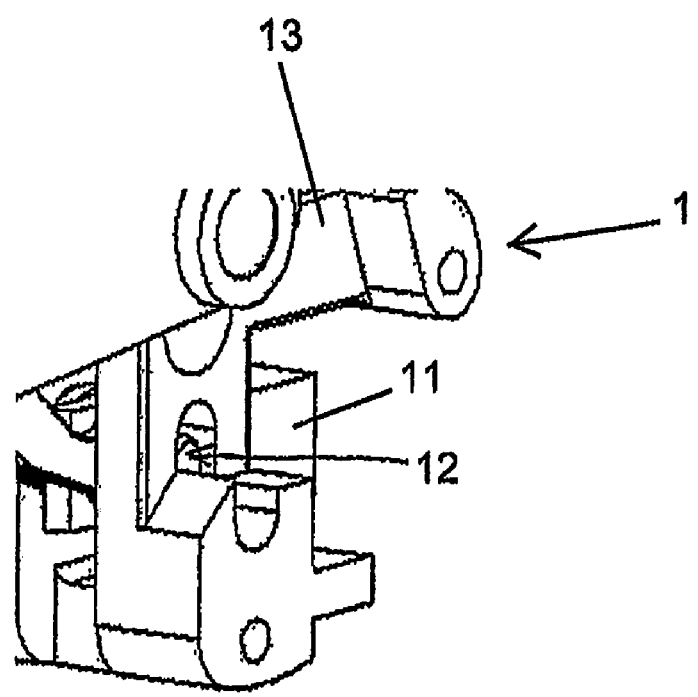
FIG. 6 is a diagram depicting a partial view of the body assembly in the preferred embodiment of the articulating mount.
Figure 8:
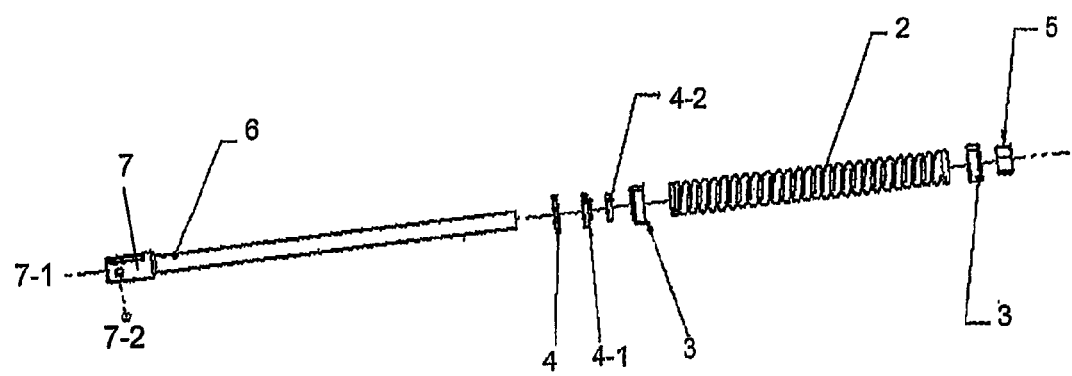
FIG. 8 is an exploded view of the spring assembly in the preferred embodiment of the articulating mount.

One preferred embodiment of the main body 1 is illustrated in FIGS. 6 and 7. The body is adjusted by a load adjustment cross piece 11. The main body 1 and adjustment cross piece 11 have holes that line up in the horizontal and vertical directions. Main body 1 and adjustment cross piece 11 accommodate a load adjustment screw 14 having a screw groove. The load adjustment screw 14 is threaded in until its screw groove exactly aligns with the hole where the dowel pin 15 goes in.

The load adjustment cross 11 is held inside the aluminum housing 13 by a load adjustment screw 14 which is held inside the aluminum housing 13 via a thru hole and dowel pin 15. The load adjustment screw 14 has a groove in it that allows it to only rotate but not move in any other direction once the dowel pin 15 has been inserted. The adjustment of the load by this positioning of screw 14 and dowel pin 15 allows for small changes in tension due to a varied load and/or loss of tension in compression spring 2 (as shown in FIG. 8) over time.

Figure 10:
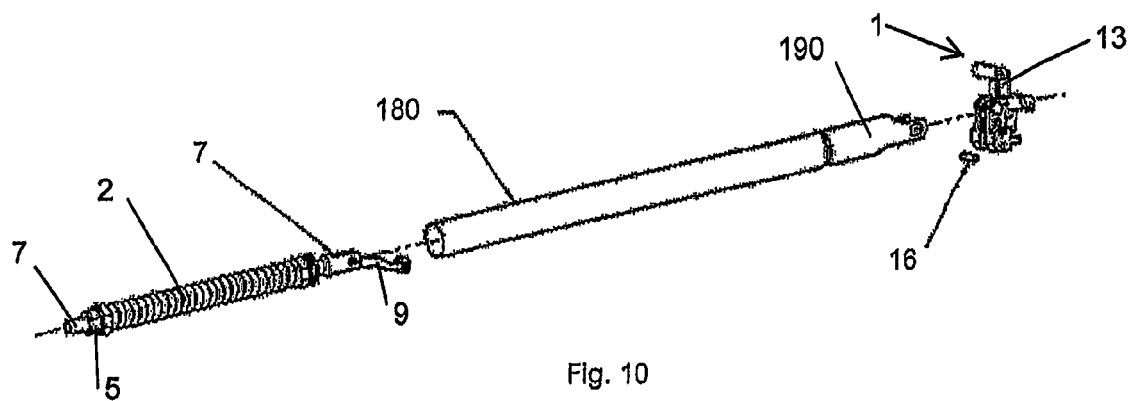
FIG. 10 is an exploded view showing the attachment of the arm and the spring assembly to the body assembly in the preferred embodiment of the invention.

FIG. 10 is an exploded view showing the attachment of the notched end 7, support arm 180 and main body 1 according to the preferred embodiment of the articulating mount 170. One end of support arm 180 is squared-off and the other end with rotation links 9 is cut out with two flanges. The cutouts at the top and bottom to allow the rotation links 9 an increased range of motion. The flanges of the cut-out end have opposing aligned holes as shown so that support arm 180 is attached to the main body 1 by shaft and nut 16. The chevrons in the rotation links 9 should be facing downwards toward the large cut out.

Preferably, support arm 180 is configured so that the threaded rod 6, notched end 7 and compression spring 2 are put into the squared-off end of, and passed through, the support arm 180 so that the rotation links are exposed at the cut-out end of the support arm 180. Alternatively, the spring arm assembly can be put into the cut-out end of the support arm 180. In such an embodiment, the support arm 180 preferably has two inwardly extending indentations or notches 190 that are perpendicular to the lengthwise direction of the support arm 180 on part of the circumference of the support arm 180. The notches 190 are positioned and sized so as to interact with the spring end bushings and the oblong spring washer 4 on the spring arm assembly. Referring to both FIG. 8 and FIG. 10, the spring arm assembly is inserted into the support arm 180 at such an angle that the flat portion of the oblong spring washer 4 lines up with the notches 190 and the spring 2 and other components pass the notches 190. Once the oblong spring washer 4 is past the notches 190, then the compression 2 and other components in the assembly are rotated 90 degrees. The notches 190 then hold the components in place at a position so that the rotation links 9 are appropriately exposed at the cut-out end of the support arm 180.

FIG. 11 shows the attachment of support arm 180 and main body into the articulating mount 170. The threaded rod 6, notched end 7 and compression spring 2 (each shown in FIG. 9) fit into the squared-off end of the support arm 180 such that the second ends of rotation links 9 are exposed at the cut-off end of the support arm 180. The second ends of rotation links 9 are attached to the load adjustment cross 11 (as shown in FIG. 7) using a rotation pin 12. The rotation links 9 (as shown in FIG. 10) and the adjustment cross piece 11 of the main body 1 are configured so that the two holes in the rotation links 9 are in line with the hole in the adjustment cross piece 11 of the main body 1. The link pivot pin 15 secures the rotation links 9 to the main body 1. FIG. 6 is a close up of the main body 1 showing the hole in the main body 1 for the link pivot pin 15 (as shown in FIG. 7). As shown in FIGS. 11 and 15, articulating mount 170 is attached to support body 160 by retainer ring washer 161, retainer ring 162, lock washer 163, and screw 164.

FIGS. 12 and 14-17 show the completed articulating mount 170. Support arm 180 also has a slotted hole 23 in it to allow for the press fit of two rotation bushings 17. The slotted hole 23 in the support arm 180 and the oblong design of the rotation bushings 17 cause the bushings 17 to remain in place and not rotate during operation. This in turn prevents excessive wear on the bushings 17 and increases reliability of the articulating mount 170.

A housing 13 is held securely in place inside the articulating mount 170 by means of three socket head cap screws 19 and lock nuts 20. The articulating mount 170 is preferably composed of steel, but may also be composed of other materials. A hole in the center of articulating mount 170 accepts the shaft 16 for support arm 160 which is held in place by retaining rings 21. The shaft 16 is preferably composed of steel, but may also be composed of other materials. On one side, the center hole has a unique cut in it to keep the shaft 16 from rotating during use. A support body 160 allowing attachment to a second arm or mount 160 is off-set from the center of the articulating mount 170 to allow for increased range of motion and is preferably a steel part welded to articulating mount 170.

This invention has been described and illustrated with reference to several preferred embodiments. While the foregoing preferred embodiments of the invention have been described and illustrated in some detail for purposes of clarity and understanding, it will be appreciated by one skilled in the art, from a reading of the disclosure that various changes in form and detail can be made upon reading and understanding the preceding specification and the drawings without departing from the scope of the invention. It is intended that the invention be construed as including all such changes insofar as they come within the scope of the appended claims or the equivalents of these claims.

What is claimed is:

1. An articulating mount, comprising:
   a support body;
   a housing secured to the support body;
   said housing encloses a main body;
   a hollow support arm, one end of said hollow support arm being pivotally connected within said main body;
   an adjustment piece that is aligned within said main body;
   said adjustment piece having a vertical opening and a horizontal opening;
   a load adjustment screw that goes through said vertical opening of said adjustment piece and through said main body;
   said load adjustment screw connects said adjustment piece to said main body;
   said load adjustment screw is held in place by way of a dowel pin and joined to said main body by an external threading on said load adjustment screw:
   a threaded rod within said hollow support arm, one end of said threaded rod is connected to said horizontal opening of said adjustment piece via rotation links; and
   a compression spring on said threaded rod, a first end of said compression spring is held by a nut on said threaded rod.

2. The articulating mount recited in claim 1, wherein said hollow support arm has an indentation on the inner surface thereof and a second end of said compression spring rests against a spring washer held in place by said indentation.

3. The articulating mount as recited in claim 2, wherein said indentation extends over only a part of the circumference of the inner surface.

4. The articulating mount as recited in claim 1, wherein said hollow support arm has an indentation on the inner surface thereof and a second end of said compression spring rests against an oblong shaped spring bushing that is interposed between the second end of said compression spring and a spring washer held in place by the indentation.

5. A load support system, comprising:
a base member supported by a plurality of wheels;
a vertical post attached to said base member;
a handle connected to said vertical post;
an articulating mount secured to the top of said vertical post;
a hollow support arm, one end of said hollow support arm being pivotally connected within a main body inside said articulating mount;
wherein said articulating mount comprises:
- a housing;
- said housing encloses said main body;
- an adjustment piece that is aligned within said main body;
- said adjustment piece having a vertical opening and a horizontal opening;
- a load adjustment screw that goes through said vertical opening on said adjustment piece and through said main body;
- said load adjustment screw connects said adjustment piece to said main body;
- said load adjustment screw is held in place by way of a dowel pin and joined to said main body by its an external threading on said load adjustment screw;
- a threaded rod within said hollow support arm, one end of said threaded rod being connected to said horizontal opening of said adjustment piece via rotation links; and
- a compression spring on said threaded rod, a first end of said compression spring is held by a nut on said threaded rod.

6. The load support system recited in claim 5, wherein said hollow support arm has an indentation on the inner surface thereof and a second end of said compression spring rests against a spring washer held in place by said indentation.

7. The load support system as recited in claim 6, wherein said indentation extends over only a part of the circumference of the inner surface.

8. The load support system as recited in claim 5, wherein said hollow support arm has an indentation on the inner surface thereof and a second end of said compression spring rests against an oblong shaped spring bushing that is interposed between the second end of said compression spring and a spring washer held in place by the indentation.

9. The load support system as recited in claim 5, wherein said base member has a sunken central portion, at least a part of said sunken central portion being lower than said plurality of wheels.

10. A load support system, comprising:
a wall or ceiling mount;
an extension arm attached to said wall or ceiling mount;
an articulating mount secured to said extension arm;
a hollow support arm, one end of said hollow support arm being pivotally connected within a main body inside said articulating mount;
wherein said articulating mount includes:
- a housing;
- said housing encloses said main body;
- an adjustment piece that is aligned within said main body;
- said adjustment piece having a vertical opening and a horizontal opening;
- a load adjustment screw that goes through said vertical opening on said adjustment piece and through said main body;
- said load adjustment screw connects said adjustment piece to said main body;
- said load adjustment screw is held in place by way of a dowel pin and joined to said main body by an external threading on said load adjustment screw;
- a threaded rod within said hollow support arm, one end of said threaded rod being connected to said adjustment piece via rotation links; and
- a compression spring on said threaded rod, a first end of said compression spring is held by a nut on said threaded rod.

11. The load support system recited in claim 10, wherein said hollow support arm has an indentation on the inner surface thereof and a second end of the said compression spring rests against a spring washer held in place by said indentation.

12. The load support system as recited in claim 11, wherein said indentation extends over only a part of the circumference of the inner surface.

13. The load support system as recited in claim 10, wherein said hollow support arm has an indentation on the inner surface thereof and a second end of said compression spring rests against an oblong shaped spring bushing that is interposed between the second end of said compression spring and a spring washer held in place by the indentation.

* * * * *